*US006156549A*

United States Patent [19]
Drewes et al.

[11] Patent Number: 6,156,549
[45] Date of Patent: Dec. 5, 2000

[54] METHOD OF DESTROYING CELLS VIA RESONANT DESTRUCTION OF INTRACELLULAR STRUCTURES

[75] Inventors: William Drewes, 21 Rimon St., Caesarea, 38900; Alon Amitay, Caesarea; Giora Rosenhouse, Haifa, all of Israel

[73] Assignee: William Drewes, Caesarea, Israel

[21] Appl. No.: 09/238,123

[22] Filed: Jan. 27, 1999

Related U.S. Application Data

[63] Continuation-in-part of application No. 08/868,625, Jun. 4, 1997, abandoned.

[51] Int. Cl.$^7$ .................................................. C12N 13/00
[52] U.S. Cl. ............................................................ 435/173.7
[58] Field of Search ............................................ 435/173.7

[56] References Cited

U.S. PATENT DOCUMENTS

| | | | |
|---|---|---|---|
| 4,315,514 | 2/1982 | Drewes et al. | 600/407 |
| 4,646,756 | 3/1987 | Watmough et al. | 607/154 |
| 4,671,254 | 6/1987 | Fair | 601/3 |
| 4,820,260 | 4/1989 | Hayden | 604/4 |
| 4,874,137 | 10/1989 | Chiba | 241/301 |
| 5,080,101 | 1/1992 | Dory | 600/439 |
| 5,143,063 | 9/1992 | Fellner | 601/3 |
| 5,149,319 | 9/1992 | Unger | 604/22 |
| 5,158,070 | 10/1992 | Dory | 601/2 |
| 5,158,536 | 10/1992 | Sekins et al. | 604/20 |
| 5,209,221 | 5/1993 | Riedlinger | 601/2 |
| 5,209,234 | 5/1993 | LaRocca | 600/439 |
| 5,230,334 | 7/1993 | Klopotek | 601/3 |
| 5,339,564 | 8/1994 | Wilson et al. | 43/124 |
| 5,409,002 | 4/1995 | Pell | 600/407 |

FOREIGN PATENT DOCUMENTS

WO 98/58701  12/1998  France.

OTHER PUBLICATIONS

F. Everett Reed, "Dynamic Vibration Absorbers And Auxiliary Mass Dampers" in Harris, C.M., Crede, C.E,. Shock and Vibration Handbook, 2nd Ed., 1976, pp. 6–1 to 6–38.

J.P. Den Hartog, Mechanical Vibrations, 4th Ed., 1956, pp. 87–90.

R.F. Steidel, Jr., An Introduction to Mechanical Vibrations, 3d Ed., 1989, pp. 291–298.

*Primary Examiner*—Jon P. Weber
*Attorney, Agent, or Firm*—Cohen, Pontani, Lieberman & Pavane

[57] ABSTRACT

A method of destroying cells selected for destruction within a host body with little to no collateral damage to healthy surrounding tissue utilizes energy to effect resonant destruction of intracellular components within the cells selected for destruction.

16 Claims, 4 Drawing Sheets

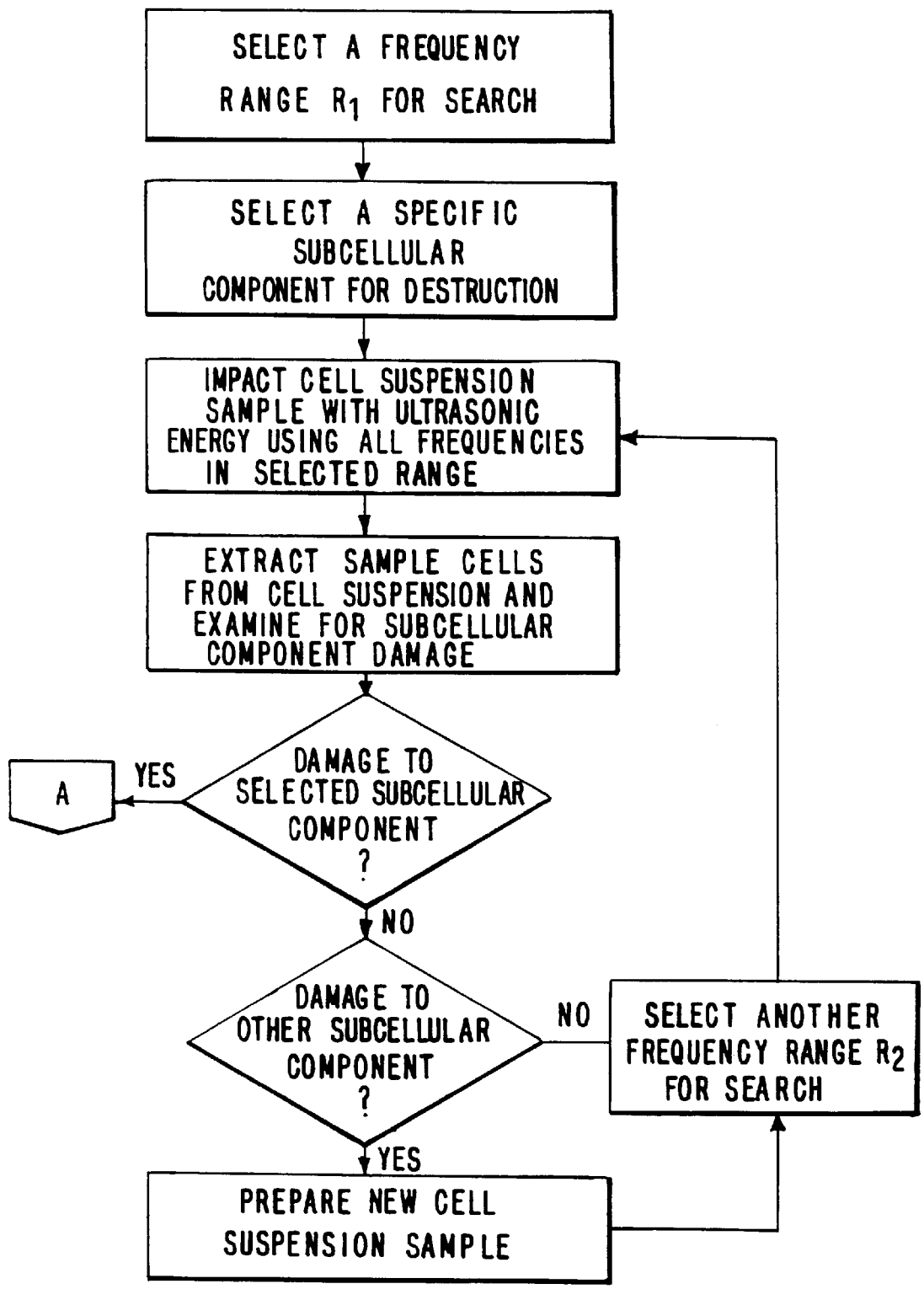

METHOD OF DESTROYING CELLS VIA RESONANT DESTRUCTION OF INTRACELLULAR STRUCTURES

CROSS REFERENCES

This application is a continuation-in-part application of a co-pending application Ser. No. 08/868,625 filed on Jun. 4, 1997.

FIELD OF THE INVENTION

This invention pertains to a method for the destruction of cells in a host body, such as cancerous tissue cells, and more specifically to the noninvasive selective destruction of such cells by the resonant destruction of intracellular components located within cells selected for destruction.

BACKGROUND OF THE INVENTION

The use of ultrasound for destroying predetermined groups of tissue cells such as tumors has been known in the art for some time. After identifying the location of cells to be destroyed in a host body, ultrasonic energy is focused on the cells to be destroyed at a level sufficient to effect tissue destruction by thermal heating. Such a technique possesses the disadvantage of potentially overheating and destroying healthy cells surrounding the cells to be destroyed since precise, selective focusing is not always possible. Moreover, such a method is useless when the target cells to be destroyed are transient, such as in the case of leukemia.

Other ultrasonic techniques involve the direct application of ultrasound to a target area by means of a vibrating surgical instrument, for example in the form of a probe. In use, such a vibrating instrument must be surgically inserted into the patient for direct application to the target cells, whereupon the target cells are destroyed by direct application of intense mechanical vibration. Such a technique also possesses the disadvantage of high risk of damage to surrounding healthy tissue, especially when the target area is small. Moreover, such a device possesses the inherent risks of surgery, including risks of infection, reaction to anaesthetic, and collateral damage and bleeding during insertion.

There has been proposed a method for destroying selected cells without damage to nonselected cells through the application of ultrasonic energy which relies on the principal of resonance of the target cells for the target cell's destruction. U.S. Pat. No. 4,315,514 teaches the selective destruction of cells by first determining the resonant frequency of the cell as a whole to be destroyed, followed by the application of ultrasonic energy at sufficient levels to cause the entire cell to resonate at its resonant frequency with sufficient energy to ensure destruction of the target cell. Such a technique bears the inherent disadvantage of a lack of assurance of destruction of all selected cells. Specifically, a selected cell's resonant frequency is determined by taking a biopsy of the selected cells, and bombarding them with ultrasonic energy over a frequency range of 0.1 megahertz (MHz) to 4 MHz. The biopsy is interferometrically monitored for motion. The resonant frequency of the cells is determined to be that frequency which causes the greatest degree of movement in the biopsy of cells. However, since the resonant frequency of cells within a selected cell type to be destroyed can vary depending, for example, on its location within surrounding tissue, the location of the nucleus within the cell, or the location of other intracellular components within the cell, the determination of a resonant frequency which causes the greatest movement in the biopsy does not necessarily ensure that the resonant frequency of all of the cancerous cells to be destroyed will be identified.

It would thus be greatly advantageous for a method to be devised which could ensure destruction of selected cells within a host body without the need for invasive surgery and with a higher degree of assurance that all cells selected for destruction will be in fact destroyed.

SUMMARY OF THE INVENTION

The present invention comprises a method for destroying selected cells, such as cancerous cells or other cells harmful to a host body, by the resonant destruction of constituent elements of the cells to be destroyed. These constituent elements are referred to herein interchangeably as intracellular or subcellular components or structures, and those terms are intended to mean the well-known internal components of a cell such as, for example, the nucleus, mitochondria, lysosomes, golgi bodies, etc. As used herein, these interchangeable terms refer to any constituent element or portion of a cell that is susceptible to resonance, as opposed to the entire cell.

Intracellular components may be placed in a state of vigorous mechanical motion when impacted with acoustic energy including, for example, ultrasonic energy at a frequency which induces resonance in the intracellular component. As is well known in the art of mechanical engineering, the mechanical response of an object to a given input driving frequency is defined by its transmissibility T where:

$$T = \frac{1}{\sqrt{\left[1 - \frac{w^2}{w_n^2}\right]^2 + [2Lw/w_n]^2}} \qquad \text{(Eq. A)}$$

In the above equation, w is the frequency of the input driving energy, $w_n$ is the resonant frequency of the object, and L is the damping coefficient of the object. Assuming, for example, that an object has a damping coefficient of 0.25, its transmissibility would decrease from a value of 4 at resonance ($w=w_n$) to 1.55 at 25% above resonance ($w=1.25w_n$). Thus, the percentage of input energy converted to mechanical energy in an object at resonance is almost three times as great as when it is driven by energy at a frequency 25% above resonance. As the damping coefficient increases, an object's transmissibility decreases. At damping ratios of 0.5 or above, the resonant effect is virtually nil.

It is also well known that objects can have several different resonant frequencies. The lowest frequency at which an object will resonate is its fundamental resonant frequency. Although the number of resonant frequencies a structure can have is theoretically infinite, the actual number of additional resonant frequencies beyond the fundamental resonance frequency is determined by the physical properties and scale of the object. Within the limits of a definite scale, the number of resonant frequencies is finite. A change in the physical properties of any component of an object will cause a change in the resonant frequencies of the object. This known phenomenon is responsible for one of the shortcomings of the prior art which sought to destroy selected cells through the inducement of resonance in the cell as a whole. Since the resonant frequency of the cell to be destroyed in the prior art was determined from a biopsy of cells, it is possible that cancerous cells of the same type would exhibit different resonant frequencies as a result of differing locations of intracellular components within the cell, as well as physical changes introduced to the cell by surrounding tissue. Thus, it is possible that within a group of cells of similar type, such cells would exhibit different resonant frequencies. Moreover, at each of these different resonant frequencies such cells will also exhibit different damping coefficients. Thus, destruction of cells by attempting to resonate the entire cell structure at a given frequency would never assuredly lead to destruction of all the cells to be destroyed.

In the present invention, this shortcoming is eliminated by determining the resonant frequencies of intracellular structures within the cells to be destroyed. Such structures are relatively unaffected by their location within the cell or by the physical position of the cell within surrounding tissue. Moreover, the corresponding resonant frequencies of those intracellular components will be significantly higher than that for the cell as a whole. In the present invention, it is contemplated that ultrasonic energy at frequencies in a range of, for example, about 5 MHz to 20 MHz will be required, frequencies which are much higher than those contemplated for resonating cell bodies as a whole.

In the present invention intracellular components are impacted with ultrasonic energy so as to lead them to destructive resonance. Intracellular components of a particular cell type will show little to no substantive variance from cell to cell, making the likelihood of destruction of all selected cells greater at a selected resonant frequency than in the case of resonating the entire cell, due to the above-noted propensity for resonant frequencies to vary on a cell to cell basis. A further advantage of the present invention is that the likelihood of achieving a 25% difference in resonant frequency between an intracellular component of a cancerous cell to be destroyed and a healthy cell is likely, since the structural differences in intracellular components between cancerous cells and normal cells are more profound than the structural difference between the cells as a whole. As demonstrated above in connection with the transmissibility equation, a variance of 25% from the resonant frequency results in a 300% reduction in conversion of energy from the source to the object being impacted with ultrasonic energy. Thus, when a resonant frequency of an abnormal cell's intracellular component(s) can be found at which the transmissibility of the abnormal cell's intracellular component(s) is sufficiently higher than the transmissibility of the surrounding healthy tissue cell's intracellular component(s), the abnormal cell's intracellular components can be caused to resonate at a frequency with sufficient intensity to destroy them, while the healthy cells, exhibiting a low transmissibility at that same frequency, will not be damaged.

Because the intracellular components of a cell are far smaller than the cell itself, the resonant frequencies of those intracellular components will be significantly higher than that of the cell as a whole. In the present invention, it is contemplated that ultrasonic energy at frequencies in a range of, for example, about 5 MHz to 20 MHz and beyond may be used.

To determine a suitable resonant frequency for destroying selected abnormal cells, one first determines the various resonant frequencies and corresponding damping coefficients of the selected cell's intracellular components. Initially, samples of the selected cells to be destroyed are taken from the host, either by surgical or needle biopsy, scraping or other technique known in the art. Cells selected for destruction are then placed in a fluid cell suspension, as is also well known in the art.

A technique for determining a resonant frequency of an intracellular structure comprises mounting a sensitive ultrasonic pickup in the fluid medium of the cell suspension. Ultrasonic energy from an energy source is then focused on the cells in suspension. The ultrasonic pick up is used to determine the amplitude of the ultrasonic energy within the fluid medium. The amplitude of the ultrasonic energy in the fluid medium can then be compared to the amplitude of the energy outputted by the source. Energy from the source will be attenuated prior to detection at the ultrasonic pickup. However, at the resonant frequencies of the intracellular structures, the attenuation will be greater, because at these frequencies the amount of energy absorbed by intracellular components will be greatest. In this way, the various resonant frequencies of an intracellular structure can be determined by identifying those frequencies at which the amplitude ratio of the source signal to the detected signal is the greatest. Generally, the frequency which exhibits the largest amplitude difference is the frequency with the highest transmissibility, and is likely, although not necessarily, the most desirable destructive frequency.

Another technique for determining a resonant frequency of an intracellular component utilizes an energy source with a controller which maintains the amplitude detected at the ultrasonic pickup at a constant value. A feedback sensor, operatively connected to the controller, is provided between the ultrasonic pickup and the energy source. The energy source is modulated to maintain a constant amplitude signal at the ultrasonic pickup. It will be apparent that when the energy absorbed by the cell suspension is high, the power required by the energy source to maintain a constant amplitude at the pick up will be correspondingly high. As described above, at the resonant frequencies of the intracellular components, the energy absorbed by the cell suspension will be greater than at other frequencies. Consequently, the resonant frequencies of the intracellular components can be determined by monitoring the power consumed by the energy source, i.e. the highest power consumption will occur at the resonant frequencies of the intracellular components. For example, a surge in power consumption by the energy source at a frequency $f_n$ will indicate that $f_n$ is a resonant frequency of the intracellular component.

Alternatively, the resonant destructive frequencies of subcellular components (e.g., a nucleus) may be determined by a binary microscopy search method described hereinbelow. First, a frequency Range $R_1$ (e.g. 10–11 Mhz) is selected in order to search for the resonant frequency of a particular subcellular component (e.g. nucleus). A sample of cancerous cells is then placed in a cell suspension and impacted with ultrasonic energy using each frequency in the frequency range. For example, a frequency sweep is performed in either ascending or descending order starting with the lowest or highest frequency in the preselected frequency range. Alternatively, the sample cells may be simultaneously impacted with ultrasonic energy having all of the frequencies in the preselected frequency range. It will be appreciated that the latter technique consumes less time than a frequency sweep because the sample cells will be impacted simultaneously by all of the frequencies of the selected frequency range. In either case, the energy amplitude and duration of exposure should be such as to expect to cause damage to the selected intracellular component.

Once the sample cells have been impacted by all of the ultrasonic frequencies of the first preselected frequency range $R_1$, the sample cells are extracted from the cell suspension and visually inspected for damage—in particular, structural damage to the selected subcellular component—using, for example, an electron microscope. If there is no observable damage to the selected subcellular component, a second search is performed in a second preselected frequency range $R_2$, preferably an immediately adjacent frequency range having the same bandwidth as that of the first frequency range $R_1$ (e.g., and adjacent 1 MHz range). In order to maintain the integrity of the sample cells in the cell suspension, a new cell suspension is prepared each time any damage to the cells is observed. This process is repeated until structural damage to the selected subcellular component is observed.

Once structural damage to the selected subcellular component is observed, the frequency range R over which such destruction was observed is then divided into two sub-ranges that are either equal or as similar in size as possible, i.e., $R_A$ and $R_B$. A new cell suspension sample containing undamaged cells is then prepared and impacted with all the frequencies of sub-range $R_A$, sample cells are extracted from the cell suspension and visually inspected for damage. If there is no observable damage to the selected subcellular component impacted by the frequencies in sub-range $R_A$, it is then assumed that sub-range $R_B$ contains the frequency which causes damage to the selected subcellular component.

The process is repeated using the sub-range containing the frequency which is either observed (i.e., $R_A$) or assumed (i.e., $R_B$) to cause damage to the selected subcellular component, until a sub-range is found which contains a defined frequency which is observed to cause damage to the selected subcellular component.

The binary microscopy search method is particularly advantageous and viable in that only a reasonable and finite number of cell suspension samples need be prepared, radiated and observed in order to locate a resonant frequency which causes structural damage to a selected subcellular structure.

Once the resonant frequencies of the target cells' intracellular structure(s) are determined by any of the aforementioned techniques, high frequency pulse techniques known in the art may be used to determine the corresponding damping coefficients of the intracellular structures. Knowledge of the resonant frequencies and corresponding damping coefficients permits resolution of the transmissibility equation described above to determine the optimum destructive resonant frequency, i.e., that frequency which will cause the greatest transfer of ultrasonic energy to mechanical energy in the object.

Another consideration in practicing the method of the present invention is to determine a transmission path through the host body to the cells selected for destruction. Such a path is selected so as to minimize attenuation and reflection losses during transmission of the source energy through the host body. Once the preferred path is selected, the transmissibility of each of the different types of normal tissue cells through which the destructive ultrasonic energy will pass must be determined for each of the selected intracellular resonant frequencies of the cells selected for destruction. Thus, resonant frequencies and corresponding damping coefficients of the intracellular structures of healthy tissue cells in the transmission path must be determined. To that end, the same techniques described for finding these coefficients in cells selected for destruction can be used. Because the variance in normal tissue cells from person to person is negligible, it will generally not be necessary to repeat these calculations for each host body being treated.

Having determined the variables discussed above, the particular resonant frequency which will be applied to the intracellular structures for causing destructive resonance therein will be that frequency at which an intracellular component that is selected for destruction exhibits a sufficiently low damping coefficient to ensure a resonant effect of sufficient magnitude, while the intracellular components of healthy cells in the transmission path correspondingly exhibit a low transmissibility at the selected frequency so as to avoid damage to the healthy tissues surrounding the cells selected for destruction.

Having determined the selected frequency, the intensity of the ultrasonic energy may be calculated. Such factors as attenuation and reflective losses along the transmission path are determined. Additionally, when a preferred medium such as water is disposed between the host body and the energy source, losses resulting from transmission through the water should also be taken into account.

In use, energy of a given intensity is directed along the preferred transmission path and focused so as to impact the cells selected for destruction. The transmission of energy continues for a period of time at the selected intensity until the intracellular structures of the selected cells mechanically vibrate at resonance to the point of destruction. As used herein the term destructive resonance is intended to mean the destruction of an intracellular component of a cell as a result of mechanical vibration induced in that intracellular structure as a result of bombardment with energy having a frequency which causes the intracellular structure to resonate at a particular one of its resonant frequencies. Because of the relatively high frequencies involved, e.g. greater than about 5 MHz, the time period during which the intracellular structure destructively resonates is minimal. Heating of neighboring healthy tissue cells will therefore be negligible.

After destruction of the selected cells utilizing the inventive technique, the destroyed cells will be carried out of the host body by its natural waste systems, though in the case of large growths surgical removal of all or a portion of the dead cell mass may be necessary. Because the abnormal cells have already been destroyed using the inventive technique, in the case of surgical removal of a large mass, and in contrast to surgical removal of live abnormal cellular growths, removal of all of the abnormal cells is not necessary, and collateral damage to surrounding healthy tissue can be minimized or avoided even when surgical removal is required.

It is contemplated that the inventive technique may be used for treating growths of abnormal cells within any host body, e.g. the body of a human, animal or plant, in accordance with the techniques disclosed herein. The inventive method is also applicable to localized abnormal growths such as those found in skin cancer patients, and also in cases where the abnormal cells are transient, such as in the case of leukemia or other diseases of the blood.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

In the drawings, which are illustrative and not to scale, and wherein like reference characters denote similar elements throughout the several views:

FIGS. 5A and 5B depict a flow chart of an alternative technique for determining subcellular resonant frequencies.

DETAILED DESCRIPTION OF THE PRESENTLY PREFERRED EMBODIMENTS

Figure 1:
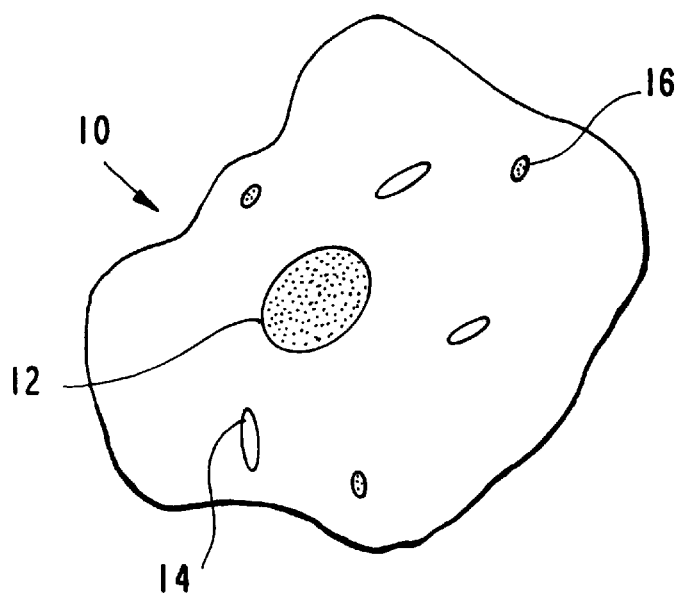
FIG. 1 is an illustrative representation of a cell depicting intracellular structures within the cell.

With initial reference to FIG. 1, there is depicted an illustrative diagram of a cell 10 having therein intracellular structures such as, by way of nonlimiting example, a nucleus 12, mitochondria 14 and lysosomes 16. These intracellular structures possess unique resonant frequencies which may be detected and used advantageously to resonantly vibrate the intracellular structure to the point of destruction. Destruction of such intracellular structures either leads to the immediate death of the cell or, alternatively, destroys the cell's ability to reproduce. In the case of abnormal cells harmful to a host body, either alternative yields effective treatment, since it is the unchecked growth of such cells which ultimately kills the host body.

Figure 2:
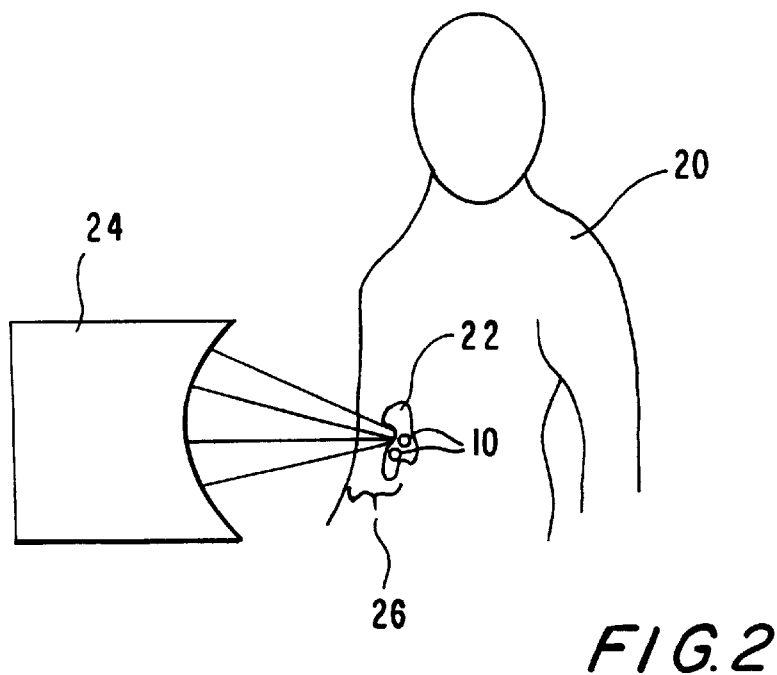
FIG. 2 is a diagrammatic illustration of an apparatus for practicing the method of the present invention.

Referring to FIGS. 1 and 2, a tumorous growth 22 made up of a mass of cancerous cells 10 having intracellular structure 12 exists in a host body 20. As used herein the term host body refers not only to a human body but to an animal or plant body as well. Tumorous growth 22 may be located within the body by any of a number of commonly known imaging techniques such as x-ray, ultrasound, magnetic resonance imaging or the like. The exact technique for locating the mass of cells destined for destruction is considered a matter of choice for the treating physician or clinician, such techniques being well known in the art.

After the cancerous cells 10 are selected for destruction, one must determine the appropriate ultrasonic frequency necessary to induce destructive resonance in intracellular structures within cells 10, such techniques being further discussed hereinbelow. To effect destruction of the selected cells, a source of energy 24 is directionally focused on tumor 22 for inducing resonant vibration in intracellular structure 12 within the selected cells 10 of tumor 22. Specifically, a focused beam of energy at the appropriate selected frequency is caused to impinge upon tumorous growth 22 so as to induce destructive resonance in intracellular structures within cells 10. The precise technique for directing focused energy on tumors 22 within host 20 from outside the body is a matter of choice for the treating technician, clinician or physician, such techniques being commonly known in the art. For instance, energy source 24 may include a piezo-electric crystal transducer coupled to a focusing lens in a manner known in the art, such device being described, for example, in U.S. Pat. No. 4,315,514, the disclosure of which is incorporated in its entirety herein by reference.

Figure 4:
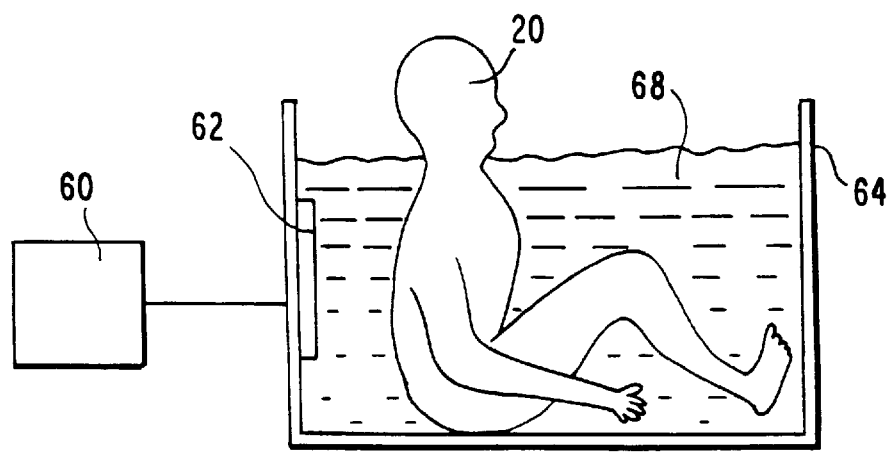
FIG. 4 is an alternate apparatus for practicing the method of the present invention.

The energy from source 24 must be directed through a desired transmission path 26 in host body 20. In order to insure that energy at the appropriate frequency is delivered to the target site within the host at the appropriate energy level and for an appropriate duration, with little to no collateral damage to healthy cells surrounding the target site, the resonance characteristics of healthy cells in the tissue along transmission path 26 must also be determined. As will be seen from the discussion below, the techniques for determining the resonant frequencies and damping coefficients of interest with respect to cells selected for destruction is the same technique used to determine the appropriate resonant frequencies and damping coefficients of healthy cells along transmission path 26. As is known in the art, if desired, a water medium, such as depicted in FIG. 4 or by any other art recognized technique, may be interposed between source 24 and patient 20 to improve coupling of the energy from source 24 to the body of patient 20, as desired.

The cells selected for destruction may be extracted from a patient's body via a surgical or needle biopsy, and a desired quantity of cells thus obtained may be placed in a fluid suspension. For selected cells which are not embedded within a host body, such as skin related carcinomas, such cell samples may be obtained by scraping. In the case of blood related disorders, cells selected for destruction may be obtained through blood sampling as opposed to biopsy. In any case, the exact method for extracting cells selected for destruction and placing them in a fluid cell suspension is a practice well known in the art and forms no part of the present invention.

Figure 3:
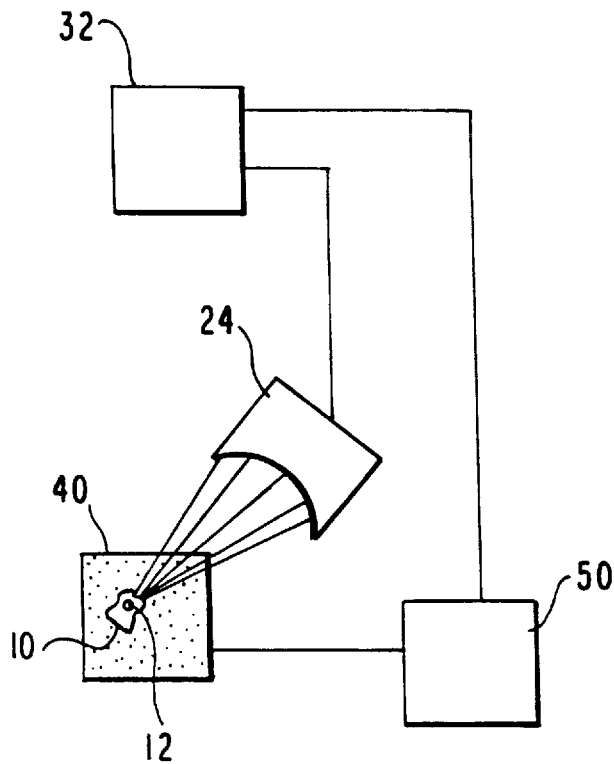
FIG. 3 is a diagrammatic illustration of an apparatus for determining subcellular resonant frequencies.

An apparatus for detecting the resonant frequency of intracellular structures is depicted in FIG. 3. As described above, a sample of cells 10 selected for destruction containing intracellular structure 12 is extracted from a host body and placed in a fluid cell suspension 40. As before, energy source 24 is focused on the cells 10 and ultrasonic energy over the above-referenced useful range is directed at the cells. An apparatus for detecting ultrasonic energy levels 50, such as, for example, a piezo-electric pickup, is connected to cell suspension 40. The amplitude of the energy emitted by energy source 24 is kept constant over the frequency range. As the ultrasonic energy impacts cells 10, energy level detector 50 senses the amplitude of the ultrasonic energy transferred to suspension 40. Computer 32 maintains a running comparison of the amplitude of the source energy emitting from energy source 24 and the energy level detected by ultrasonic energy detector 50. Resonance is essentially a transfer of energy from a transmitting medium to a resonating object. At the point at which an intracellular structure 12 in cells 10 resonates, energy will be transferred from energy source 24 through fluid medium 40 to intracellular structure 12 and converted to mechanical vibratory energy, resulting in a corresponding drop in the amplitude of the energy detected by energy detector 50. Of course, since the sample comprises a number of cells 10, the drop in energy detected by the detector 50 is the result of the amplitude energy absorbed by all of the cell 10 in the sample, and this drop in energy will be sufficient for destruction by detector 50. The difference between the amplitude of the energy emitted by source 24 and the amplitude detected by energy detector 50 is recorded by computer 32. The various resonant frequencies present within the frequency range utilized are determined by identifying the frequencies at which the drop in energy level detected by energy detector 50 is greatest. Said another way, the resonant frequencies of an intracellular structure 12 are determined by identifying the frequencies at which the difference between the amplitude of energy source 24 and energy level detected by energy detector 50 is at its greatest. Generally, the frequency which exhibits the largest amplitude difference is the frequency with the highest transmissibility, and is likely, although not necessarily, the most desirable destructive frequency.

Another technique for determining a resonant frequency of an intracellular component utilizes an energy source with a controller which maintains the amplitude detected at the ultrasonic pickup at a constant value. A feedback sensor, operatively connected to the controller, is provided between the ultrasonic pickup and the energy source. The energy source is modulated to maintain a constant amplitude signal at the ultrasonic pickup. It will be apparent that when the energy absorbed by the cell suspension is high, the power output required by the energy source to maintain a constant amplitude at the ultrasonic pickup will be correspondingly high. At the resonant frequencies of the intracellular components, the energy absorbed by the cell suspension will be greater than at other frequencies. Consequently, the resonant frequencies of the intracellular components can be determined by monitoring the power consumed by the energy source, i.e., the highest power consumptions will occur at the resonant frequencies of the intracellular components. For example, a surge in power consumption by the energy source at a frequency $f_n$ will indicate that $f_n$ is a resonant frequency of the intracellular component.

Alternatively, the resonant destructive frequencies of subcellular components (e.g., a nucleus) may be determined by a binary microscopy search method described hereinbelow. First, a frequency range $R_1$ (e.g. 10–11 MHz) is selected in order to search for the resonant frequency of a particular subcellular component (e.g. nucleus). A sample of cancerous cells is then placed in a cell suspension and impacted with ultrasonic energy using each frequency in the frequency range. For example, a frequency sweep is performed in either ascending or descending order starting with the lowest or highest frequency in the preselected frequency range. Alternatively, the sample cells may be simultaneously impacted with ultrasonic energy having all of the frequencies in the preselected frequency range. It will be appreciated that the latter technique consumes less time than a frequency sweep because the sample cells will be impacted simultaneously by all of the frequencies of the selected frequency range. In either case, the energy amplitude and exposure duration should be such as to expect to cause damage to the selected intracellular component.

Once the sample cells have been impacted by all of the ultrasonic frequencies of the first preselected frequency range $R_1$, the sample cells are extracted from the cell suspension and visually inspected for damage—in particular, structural damage to the selected subcellular component—using, for example, an electron microscope. If there is no observable damage to the selected subcellular component, a second search is performed in a second preselected frequency range $R_2$, preferably an immediately adjacent frequency range having the same bandwidth as that of the first frequency range $R_1$ (e.g. and adjacent 1 MHz range). In order to maintain the integrity of the sample cells in the cell suspension, a new cell suspension is prepared each time damage to the cells is observed. This process is repeated until structural damage to the selected subcellular component is observed.

Once structural damage to the selected subcellular component is observed, then the frequency range R over which such destruction was observed is divided into two sub-ranges that are either equal or as similar in size as possible, i.e., $R_A$ and $R_B$. A new cell suspension sample containing undamaged cells is then prepared and impacted with all the frequencies of sub-range $R_A$, the sample cells are extracted from the cell suspension and visually inspected for damage. If there is no observable damage to the selected subcellular component impacted by the frequencies in sub-range $R_A$, it is assumed that sub-range $R_B$ contains the frequency which causes damage to the selected subcellular component.

The process is repeated using the sub-range containing the frequency which is either observed (i.e., $R_A$) or assumed (i.e., $R_B$) to cause damage to the selected subcellular component, until a sub-range is found which contains a defined frequency which is observed to cause damage to the selected subcellular component.

The binary search method is particularly advantageous and viable in that only a reasonable and finite number of cell suspension samples need be prepared, radiated and observed in order to locate a resonant frequency which causes structural damage to a selected subcellular structure. Also, this technique relies on visual observation of destruction of the targeted subcellular component, thereby assuring that the selected frequency is effective for its intended purpose. Of course, the efficacy of the resonant frequencies identified by the other techniques described herein may also be verified by observations using election microscopy.

Figure 5B:
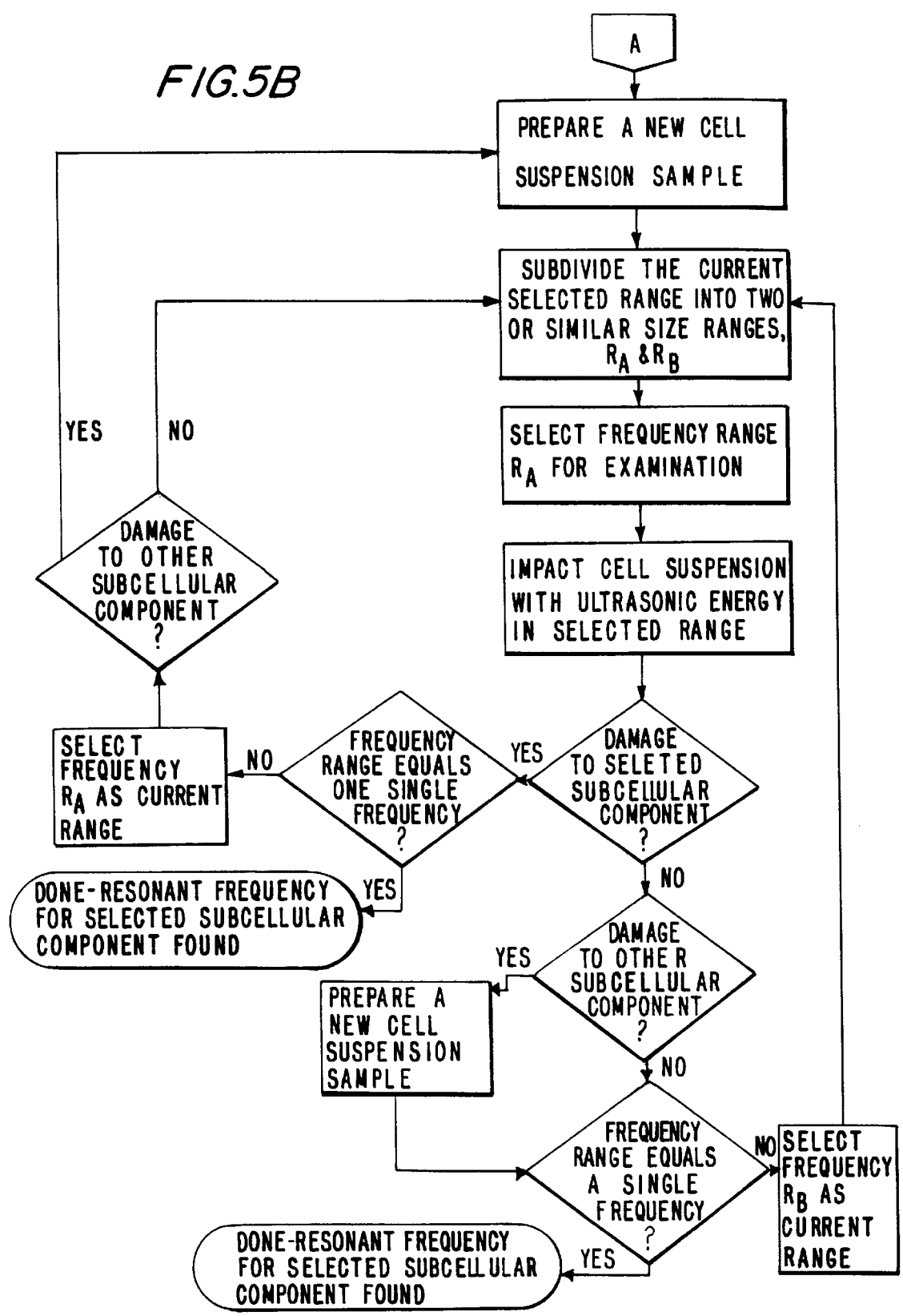

FIGS. 5A and 5B illustrate the binary search method in the form of a flow chart.

Of course, those skilled in the art may utilize alternate techniques for determining the resonant frequency of selected subcellular components in cells to be destroyed, as a matter of choice.

Once the potentially useful resonant frequencies of the intracellular component 12 of sampled cell 10 are known, the damping coefficients of the intracellular structure at those frequencies are determined. Because of the frequencies involved, it is presently preferred to employ high frequency pulse techniques known in the art to determine the damping coefficients. For example, a cell sample may be exposed to pulses of ultrasonic energy at a predetermined intensity at one of the resonant frequencies. As the pulse penetrates the specimen, the intensities of the returning echo pulses reflected from the rear face of the specimen are detected. As is well known to those skilled in the art, the damping coefficient of the intracellular structures at the resonant frequency under consideration is then determinable from the decay rate of the echo pulses.

To determine the damping coefficients at the other resonant frequencies of the intracellular component 12 of cell 10, the procedure is simply repeated with suitable adjustment of the pulse frequency. For reasons that will be apparent hereinafter, the damping coefficients at each resonant frequency are preferably stored in the computer 32.

Once the resonant frequencies and corresponding damping coefficients of the intracellular structures selected for destruction are known, the energy intensity required to destroy these structures at each resonant frequency is determined. This determination is readily made by stepping the source 24 to each resonant frequency of the intracellular structure 12, such stepping preferably being carried out by the computer 32 which may be preprogrammed for this function. At each resonant frequency, the intensity of the signal from the source 24 is gradually increased until destruction of the intracellular structure 12 in cell 10 is detected. Such destruction may be detected, for example, by visual observation through a microscopic element (not shown) or other viewing technique known in the art. Whatever technique is employed, the intensity level of the ultrasonic energy from source 24 at the point of destruction is recorded and preferably stored in the computer 32. A new group of cells 10 is then substituted whereupon the procedure is repeated at the next resonant frequency, and so on, until the energy intensity required to effect destructive resonance of the intracellular structure at each resonant frequency is recorded.

Of course, the actual intensity of the energy required to destroy intracellular structures within the host 20 will be higher than the intensity required to destroy those in suspension 40. One reason for this difference is that energy will be lost by attenuation and reflection as the energy beam passes through intervening body tissues before striking the abnormal cells 10 in the host 20. In view of these losses, it is generally preferably to position the patient such that the travel distance of the source beam through the body is minimized. However, specific situations might require using a slightly longer path. For example, in view of the relatively high losses encountered at bone-tissue interfaces, and during transmission through bone itself, longer travel distances which avoid bones may be desirable.

To compensate for the attenuation and reflection losses encountered during transmission through intervening body tissue, the actual magnitude of these losses must be determined. To do so, it is first necessary to select a transmission path 26 through patient 20 to the cells 10. Once the path 26 is selected, the actual attenuation and reflection losses resulting from transmission through that path may be calculated. The attenuation per unit distance for high frequency transmissions through various body tissues as a function of frequency may be calculated for various body tissues using equations known in the art, and available, for example, in Harris & Crede's *Shock and Vibration Handbook*, Second Edition, McGraw Hill, 1976, the content of which is incorporated herein by reference in its entirety. Of course such losses may also be obtained by direct empirical investigation, in a manner known in the art.

Once the travel distance through each type of body tissue in the transmission path 26 is known, the total attenuation losses may be calculated. The distance traveled through each intervening body tissue may be determined, for example, by x-ray or pulse imaging techniques. The attenuation losses are preferably calculated at each resonant frequency of the intracellular structure selected for destruction.

Information sufficient to calculate losses resulting from reflection at issue interfaces in the selected path is also available. Thus, the fraction of energy $a_r$ reflected at an interface between two media is given by the equation:

$$a_r \left[ \frac{Z_2 - Z_1}{Z_2 + Z_1} \right]^2 \quad \text{(Eq. B)}$$

wherein $Z_1$ is the acoustic impedance of the first medium and $Z_2$ is the acoustic impedance of the second medium. The acoustic impedance Z of a given medium is equal to pc where p is the density of the medium and c is the velocity of sound through that medium.

The acoustic impedances for various body tissues may be calculated for various body tissues using equations known in the art, and available, for example, in Kinsler & Frey's *Fundamentals of Acoustics*, Second Edition, John Wiley & Sons, 1962, the content of which is incorporated herein by references in its entirety. Of course such impedances may also be obtained by direct empirical investigation, in a manner known in the art.

Once the tissue interfaces in the selected transmission path are identified, the fraction of the initial energy lost during transmission as a result of reflection losses is determined by summing the losses at each successive interface as calculated from Equation B. The different tissue interfaces may also be identified, for example, by employing X-ray or pulse echo imaging techniques. Inasmuch as the acoustic impedance of most materials, including body tissues, is relatively constant at frequencies above 1 megahertz, it is not necessary to recalculate reflection losses for each resonant frequency of intracellular structure.

Preferably, the computer 32 is provided with a data base comprising the impedance and attenuation characteristics of the various body tissues. The computer may then be programmed to calculate the attenuation and reflection losses for any given frequency and transmission path, such programming being well within the capabilities of one skilled in the computer arts. Indeed, if, as presently preferred, the data base of the computer 32 is augmented with information defining the anatomy of the patient 20, the computer may be programmed to determined the optimum transmission path, i.e., the path resulting in the minimum energy loss, such programming also being within the capabilities of the skilled art worker once this description is known.

Two additional factors must be taken into account to determine the actual intensity required to destroy the intracellular structures of abnormal cells 10 in the patient 20. One is energy losses encountered during transmission through any intervening medium, such as water. These losses comprise both attenuation losses during transmission and reflection losses at the water-skin interface. Inasmuch as the attenuation characteristics and acoustical impedance of water are well known, these losses are readily calculated.

The second factor which must be taken into account is the losses resulting from transmission through the air medium between the energy source 24 and the cell suspension 40. The losses occasioned during transmission through the air medium are due to attenuation losses as well as reflection losses at the air-cell interface. Inasmuch as the attenuation characteristics and acoustical impedance of air are well known, these losses are also easily calculated. Preferably, calculation of the attenuation and reflection losses resulting from transmission both through the water and air medium are carried out by the computer 32, which may be programmed for this function, such programming being well within the capabilities of the skilled art worker.

At this point, information sufficient to calculate the actual energy intensity required to destroy intracellular structure 12 in patient 20 at each resonant frequency of the cells is known, this intensity being equal to the intensity required to destroy the intracellular structure 12, adjusted to compensate for transmission through the air and water media, and the intervening body tissue. These calculations are preferably carried out by the computer 32 which may be preprogrammed for this function. The results are preferably stored in the computer 32 for subsequent use.

The intensities and frequencies of a plurality of ultrasonic beams potentially useful for destroying intracellular structures in cells 10 are now known. Of these, the optimum destructive beam is selected. This requires consideration of two factors. The first is the damping coefficient of the target intracellular structure at the destructive frequency selected. Thus, as is apparent from Equation A, the resonant effect imparted to the selected intracellular 12 within selected cell 10 at a particular frequency is a function of the damping coefficient of the structure 12 at that frequency. It can be shown from Equation A that if the damping coefficient is 0.5 or higher, the resonant effect is virtually nil. To insure that a sufficient resonant effect is imparted, the damping coefficient of the selected intracellular structure at the selected frequency should be less than 0.5 and preferably 0.2 or less. Assuming a damping coefficient of 0.2 or less is desired, any potentially destructive resonant frequency at which the selected intracellular structure exhibits a damping coefficient higher than 0.2 may be eliminated.

The second factor in determining the proper destructive frequency is the potential for damage to intervening body tissue. Thus, if the destructive beam selected for resonating the selected intracellular structure imparts a significant resonant effect to the intervening body tissue as well, it may result in damage to that tissue. Such a result is clearly undesirable. From Equation A, it will be apparent that once the resonant frequencies and corresponding damping coefficients of the various intervening body tissues are known, the resonant effect that would be imparted to those tissues at each potentially destructive resonant frequency may be determined. The resonant frequencies and corresponding damping coefficients of intervening body tissue may be determined, for example, by employing the same techniques described hereinabove for determining the resonant frequencies and damping coefficients of intracellular structures of selected cells 10.

In any event, once the resonant effect that would be imparted to the various intervening body tissues at each potentially destructive resonant frequency is known, the potentially destructive frequency imparting the least resonant effect to the intervening body tissues is preferably the frequency selected. In practice, this selection will preferably be performed by the computer 32, which may be preprogrammed for this purpose. Such programming is well within the capabilities of the skilled art worker once this description is known.

In a modified procedure, the technique for selecting a destructive beam that will avoid significant damage to intervening body tissue may be somewhat simplified. Thus, it may be shown from Equation A that when there is a difference of approximately 25% or more between the input frequency w and the resonant frequency $w_n$ of the object, the resonant effect imparted to the object is virtually non-existent. Accordingly, damage to intervening body tissue may be avoided by selecting a destructive resonant frequency exhibiting a difference of 25% or more from the resonant frequencies of the intervening body tissues.

Whatever technique is employed, once obtained the energy source 24 is positioned to focus energy at the frequency and intensity of the selected destructive beam. The transmission from the source 24 is continued for a duration of time sufficient to destroy the intracellular structure of the selected cells. A good approximation of the time duration required is available from a comparison with the time required to destroy the intracellular structure 12 when in suspension 40, as discussed above.

Where the abnormal cells 10 define a growth 22 of some thickness, the intensity of the ultrasonic transmission must be increased to insure destruction of the cells farthest from the source 24 in view of the attenuation losses resulting from transmission of the beam through the growth itself. Alternatively, the beam path through the patient may be altered as the destruction process proceeds.

If the target growth 22 occupies a volume in excess of the focal zone of the source 24 the ultrasonic beam may be scanned over the target area to insure that all selected intracellular structures 12 in the cells 10 are destroyed. Such scanning can be effected in an art-recognized manner once the location of the abnormal growth has been determined as described hereinabove. Preferably, such scanning is carried out automatically by the computer 32, in which data defining the locus of the growth 22 has been stored. Assuming the computer 32 is provided with a data base defining the anatomy of the patient 20, the computer may be programmed to continuously adjust the intensity of the ultrasonic transmission to compensate for the continuous changes in the transmission path during scanning. It will be apparent, however, that destruction of the intracellular structures 12 of cells 10 according to the present invention does not depend on precise focusing of the destructive beam. Thus, because the present invention relies upon the phenomenon of resonance rather than heating to destroy the abnormal cells 10, impacting the adjacent healthy cells by the beam will not destroy those cells. Therefore, it is sufficient if the beam is scanned to impact the entire abnormal growth, without particular regard to whether or not the neighboring healthy cells are impacted in the process.

Where the number of target cells 10 is not excessive, it is contemplated that the dead cells will be carried out of the body by the body's normal waste system. However, where a large growth is involved, it may be necessary to surgically remove the dead cells. However, even where surgical removal is required, the technique described hereinabove is not redundant since it is well known that conventional surgical techniques often do not result in complete removal of the abnormal cells. In fact, to avoid this problem surgeons often remove healthy surrounding tissue.

Where surgery is used to remove cells destroyed by the method and apparatus of the present invention, healthy surrounding tissue may be left intact. Any dead abnormal cells left in the body as a result will be carried out by the body's waste system. In any event, inasmuch as they have already been destroyed, such cells will not cause any further damage to the body.

Thus far, the method and apparatus of the present invention have been described in connection with destruction of a localized abnormal cell growth. However, as will now be described, the technique is also suited for destroying non-localized and transient abnormal cells growths as well. For example, some cancers are characterized by excessive or abnormal cells in the blood. In the case of leukemia, there is an excess of leukocytes in the blood. Because these leukocytes are transient, conventional surgical techniques are useless.

To destroy the excess leukocytes utilizing the apparatus and method of the invention, it is necessary, as heretofore described, to first determine the resonant frequencies and corresponding damping coefficients of selected subcellular components of the leukocytes. An impact site for the ultrasonic radiation is then chosen and the losses resulting from transmission through the intervening body tissue are calculated. Using the techniques described hereinabove, the optimum resonant frequency for destroying the selected intracellular structure within the leukocytes is then selected taking into account the need to avoid damage to intervening body tissue. The required intensity for the destructive beam may then be determined.

Inasmuch as blood is continuously circulated throughout the body, it is not necessary to impact the entire body with ultrasonic radiation to effect destruction of the leukocytes. Rather, one or more sites may be selected and the ultrasonic bursts continued until sufficient leukocytes have been destroyed. The sites are preferably chosen to minimize the intervening body tissue. Moreover, a plurality of ultrasonic energy sources 24 may be employed, each coupled to a stereotaxic device to accommodate scanning and focus. Alternatively, the blood may be circulated outside the body for impacting the blood with energy from source 24, thereby avoiding the continuous impacting of intervening body tissue.

Skin cancer, often found over several areas of the body, may also be effectively treated by the method and apparatus of the invention. Following the teachings of the present invention, the optimum destructive beam is selected. Inasmuch as there is no intervening tissue between the skin cancer cells and the energy source 24, and thus minimal transmission losses, a precisely focused beam of radiation is not required. Instead, and as shown in FIG. 4, the patient 20 may be submerged in a tank 64 filled with a suitable liquid, such as water 68. As shown, a piezoelectric crystal 62 is secured against one sidewall of the tank 62 and is driven by ultrasonic signal generator 60. The generator 60 is then adjusted to drive the crystal at the selected frequency with sufficient intensity to destroy the cancerous cells. To insure impacting of the entire body with ultrasonic energy, it may be necessary to reposition the patient from time to time.

Those skilled in the art will appreciate that the preferred method and apparatus of the present invention as described hereinabove may be modified once this description is known. For example, the ordering of the steps of the method of the invention may be varied. In one such variation, the step of selecting the preferred transmission path through the patient 20 to the cells 10 is carried out first. The resonant frequencies are then determined, whereupon some of them may be immediately eliminated as a suitable destructive frequency because they impart too great a resonant effect to the intervening body tissue. The damping coefficients at the remaining resonant frequencies are then calculated, and the resonant frequency at which the selected intracellular structure exhibits the lowest damping coefficient selected as the optimum frequency for the destructive beam. Thereafter, it is only necessary to determine the intensity at the selected frequency. It will also be apparent that although the method and apparatus of the invention have been particularly described in connection with the destruction of selected cells in human patients, use with all manner of living things, i.e. animals, plants, microorganisms, etc. is possible. Accordingly, in the claims, the term "host" should be understood to include all such living things.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. A method of destroying selected cells in a host comprising the steps of:

determining a resonant frequency of a selected subcellular component of said selected cells; and directing acoustic energy from an energy source at said selected subcellular component, at a selected frequency which causes said selected subcellular component to resonate at said determined resonant frequency, for a duration and at an amplitude level sufficient to cause resonant destruction of said selected subcellular component, thereby causing destruction of said selected cell.

2. The method according to claim 1, further comprising the steps of:

determining a plurality of resonant frequencies of a selected subcellular component of said selected cells;

determining a transmission path for said acoustic energy;

determining whether non-selected cells are present along said transmission path; and selecting as said selected frequency a frequency which causes said selected cell subcellular component to destructively resonate at one of said plural determined resonant frequencies while causing no irreversible harm to said non-selected cells in said transmission path.

3. The method of claim 2, wherein said step of selecting said selected frequency further comprises the steps of:

determining damping coefficients of said selected cell subcellular components at each of said plural resonant frequencies so as to determine the transmissibility of said selected cell subcellular component at each of said plural resonant frequencies;

determining a plurality of resonant frequencies and corresponding damping coefficients of a selected subcellular component of said non-selected cells so as to determine the transmissibility of said non-selected cell subcellular component at each of said plural resonant frequencies of said non-selected cell subcellular component; and selecting as said selected frequency that frequency for which the determined transmissibility value for said selected cell subcellular component is higher than the determined transmissibility value for said non-selected cell subcellular component.

4. The method of claim 3, further comprising the steps of:

determining transmission losses along said transmission path; and adjusting one of said duration and said amplitude level to compensate for said determined transmission losses.

5. The method of claim 1, wherein the step of determining a resonant frequency further comprises the steps of:

placing a sample of said selected cells in a fluid suspension;

directing acoustic energy of preselected amplitude, at a frequency which varies over a preselected frequency range, at said sample in said cell suspension;

detecting the amplitude of said directed acoustic energy in said fluid suspension; and identifying the frequency at which there exists the greatest difference between the detected amplitude and said preselected amplitude.

6. The method of claim 1, further comprising the step of disposing a coupling medium between said energy source and said selected cells.

7. The method of claim 1, wherein the resonant frequency of said selected subcellular component is determined by a binary microscopy search method.

8. The method of claim 7, wherein said binary microscopy search method comprises the steps of:

(a) selecting a frequency range within which a search for a resonant frequency of the subcellular component is to be conducted;

(b) placing a sample of said selected cells in a fluid suspension;

(c) impacting said sample in said fluid suspension with energy at frequencies in said frequency range;

(d) examining at least one of said selected cells from said impacted sample for damage to said selected subcellular component;

(e) if said examining step reveals no damage to said subcellular component, selecting another frequency range and repeating steps (b) through (d) for said another frequency range until said examining step reveals damage to said selected subcellular component, preparing another sample for step (b) when step (d) reveals damage to any subcellular component in said at least one of said selected cells, and selecting as a frequency search range said frequency range at which said examining step reveals damage to said subcellular component;

(f) subdividing a frequency search range into two ranges, $R_A$ and $R_B$;

(g) selecting one of $R_A$ and $R_B$ as a frequency search range and repeating steps (b) through (d) for said one of $R_A$ and $R_B$;

(h) if the examining step reveals no damage to said selected subcellular component, subdividing the other of said $R_A$ and $R_B$ ranges into two ranges, selecting one of said two subdivided ranges as a frequency search range and repeating steps (b) through (d), and preparing another sample for step (b) when step (d) reveals damage to any subcellular component in said at least one of said selected cells;

(i) if the examining step reveals damage to said selected subcellular component from the acoustic energy, subdividing said one of said $R_A$ and $R_B$ into two ranges, then selecting one of said two subdivided ranges as a frequency search range and repeating steps (b) through (d) using another sample; and (j) repeating steps (f) through (i) until step (i) for the frequency search range identifies a resonant frequency of the selected subcellular frequency.

9. The method of claim 8, wherein in step (f) the ranges $R_A$ and $R_B$ are of substantially equal size.

10. The method of claim 8, wherein in step (h) the two subdivided ranges are of substantially equal size.

11. The method of claim 8, wherein in step (i) the two subdivided ranges are of substantially equal size.

12. The method of claim 8, wherein step (c) includes varying the frequency of the energy from one end of said frequency range to another end of said frequency range.

13. The method of claim 8, wherein step (c) includes impacting said sample with energy having all of the frequencies of said frequency range.

14. The method of claim 8, wherein said acoustic energy from said energy source includes ultrasonic energy.

15. The method of claim 1, wherein the step of determining a resonant frequency further comprises the steps of:

placing a sample of said selected cells in a fluid suspension;

providing an energy source for impacting said sample with energy having frequencies in a preselected frequency range;

detecting the energy in said fluid suspension;

maintaining the detected energy at a constant amplitude by controlling the energy outputted by the energy source;

monitoring power consumption of the energy source as a function of the frequencies of the energy impacting said sample; and identifying a resonant frequency of the subcellular component as a frequency at which power consumed by the energy source exhibits a peak.

16. The method of claim 15, wherein said acoustic energy from said energy source includes ultrasonic energy.

* * * * *